(12) United States Patent
Gerlach et al.

(10) Patent No.: US 7,101,824 B2
(45) Date of Patent: Sep. 5, 2006

(54) PREPARATION OF RUTHENIUM/IRON CATALYSTS SUPPORTED ON CARBON

(75) Inventors: Till Gerlach, Ludwigshafen (DE); Hans-Georg Göbbel, Kallstadt (DE); Frank Funke, Frankenthal (DE); Klaus Ebel, Lampertheim (DE); Ekkehard Schwab, Neustadt (DE); Signe Unverricht, Mannheim (DE); Reinhard Körner, Frankenthal (DE); Lisa Lobree, Philadelphia, PA (US)

(73) Assignee: BASF Aktiengellsellschaft, Ludwigshafen (DE)

( * ) Notice: Subject to any disclaimer, the term of this patent is extended or adjusted under 35 U.S.C. 154(b) by 490 days.

(21) Appl. No.: 10/309,115

(22) Filed: Dec. 4, 2002

(65) Prior Publication Data

US 2003/0149310 A1    Aug. 7, 2003

(30) Foreign Application Priority Data

Dec. 7, 2001  (DE) ............................... 101 60 144
Jul. 31, 2002  (DE) ............................... 102 35 064

(51) Int. Cl.
*B01J 31/00* (2006.01)
*C07C 29/16* (2006.01)
*C07C 33/04* (2006.01)

(52) U.S. Cl. ....................... 502/185; 568/874; 568/883

(58) Field of Classification Search ............... 502/185; 568/874, 883
See application file for complete search history.

(56) References Cited

U.S. PATENT DOCUMENTS

| 3,284,517 | A | 11/1966 | Rylander et al. ............. 260/638 |
| 4,465,787 | A | 8/1984 | Horner et al. ............... 502/185 |
| 4,536,347 | A | 8/1985 | Horner et al. ............... 260/465 |
| 5,939,589 | A | 8/1999 | Kaibel et al. ............... 568/568 |
| 6,150,564 | A | 11/2000 | Brocker et al. ............. 568/462 |

FOREIGN PATENT DOCUMENTS

| EP | 0 071 787 | 2/1983 |
| EP | 947 943 | 10/1999 |
| EP | 0 993 866 | 4/2000 |
| FR | 2 791 672 | 10/2000 |
| WO | WO 99/43430 | 9/1999 |

OTHER PUBLICATIONS

J.ofOilTech.Assoc.Ind. Paulose et al. 88-91.
J.ofOilTech.Assoc.Ind. Paulose et al. 88-91 (1974).

*Primary Examiner*—Porfirio Nazario-Gonzalez
(74) *Attorney, Agent, or Firm*—Novak Druce DeLuca & Quigg

(57) ABSTRACT

The present invention relates to a process for the preparation of iron-doped ruthenium catalysts supported on carbon, and their use for the selective liquid phase hydrogenation of carbonyl compounds to give the corresponding alcohols, in particular for the hydrogenation of citral to give geraniol or nerol or of citronellal to give citronellol.

14 Claims, 1 Drawing Sheet

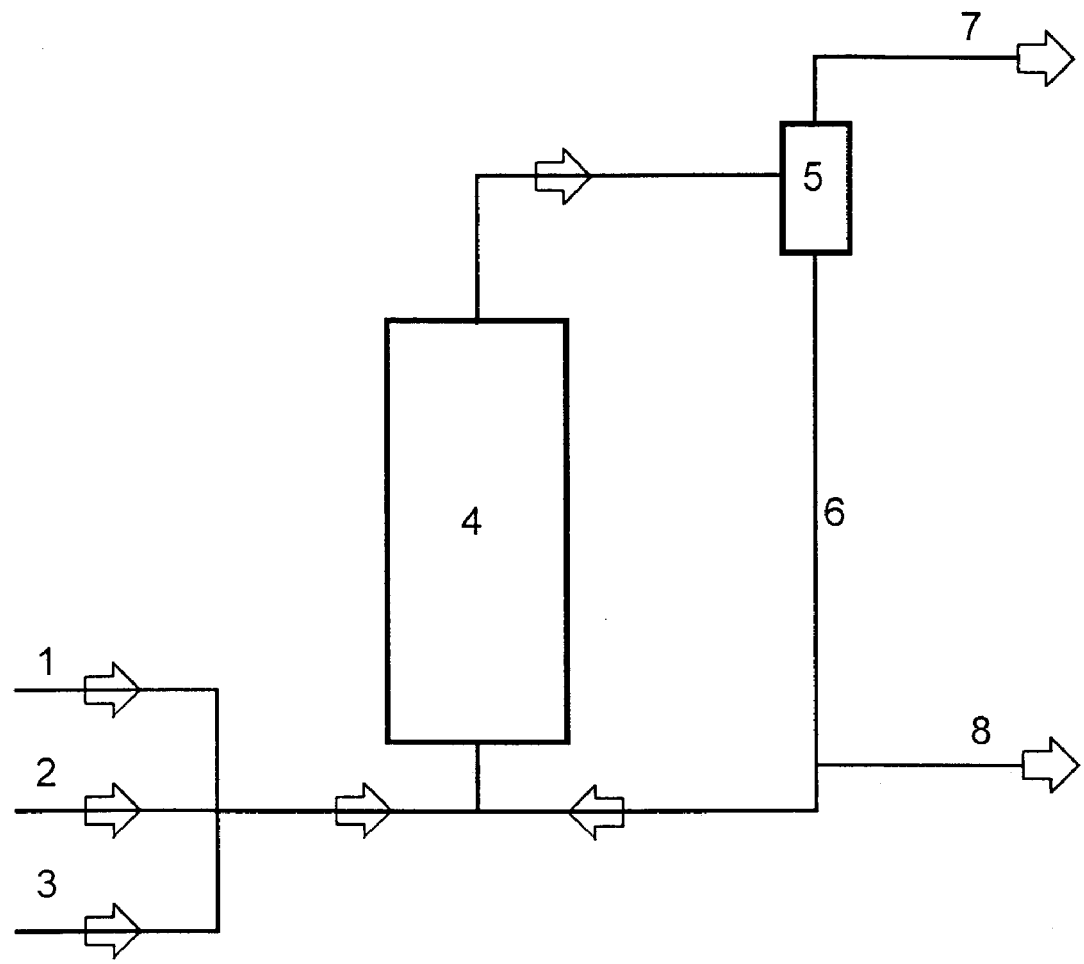
1 Hydrogen feed
2 Citral feed
3 TMA/methanol feed
4 Reactor
5 Separator
6 Circulation
7 Effluent

PREPARATION OF RUTHENIUM/IRON CATALYSTS SUPPORTED ON CARBON

The present invention relates to a process for the preparation of iron-doped ruthenium catalysts supported on carbon, and their use for the selective liquid phase hydrogenation of carbonyl compounds to give the corresponding alcohols, in particular for the hydrogenation of citral to give geraniol or nerol or of citronellal to give citronellol.

The prior art discloses various processes for the preparation of catalysts. The processes differ mainly by the preceding steps used for the active components or by the means of precipitation of the active components on the carbon support.

EP 071 787 discloses ruthenium/iron/carbon hydrogenation catalysts, and also their preparation and use for the selective hydrogenation of unsaturated carbonyl compounds. The preparation of the Ru/Fe/carbon catalyst used is carried out by saturation of activated carbon powder with ruthenium chloride solution, drying and subsequent mixing with iron oxide. The catalyst is reduced with hydrogen at 500° C.

However, the use of chlorides presents technical problems, since chloride is highly corrosive. Saturation and drying of the active components must therefore be carried out in expensive, corrosion-resistant apparatus. The reduction results in the formation of HCl, which can damage the reduction oven and chloride can remain on the catalyst, which may result in corrosion in the production reactor when the catalyst is used for hydrogenation.

If a nitrate salt of ruthenium is used instead of chloride, this can lead to safety problems, since nitrate/carbon mixtures can be explosive. A further disadvantage of the process described is the subsequent doping with $Fe_2O_3$, which requires a further process step.

The prior art also discloses various hydrogenation processes for $\alpha,\beta$-unsaturated carbonyl compounds. However, it is difficult to obtain high selectivities for the corresponding alcohols by the processes described and the catalysts used. The hydrogenation of citral can, for example, result in the hydrogenation of olefinic double bonds as well as the aldehyde group, or only of the double bond conjugated to the aldehyde group, so that, as well as the unsaturated alcohols geraniol and nerol, byproducts such as citronellol or citronellal can be formed.

M. M. Paulose et al., J. Oil Technol. Assoc. India 1974, 6, 88–91, describe a continuous fixed bed process for the selective hydrogenation of citral. Copper/chromium/cadmium catalysts were used. In order to obtain sufficient citral conversions, the reaction must be carried out at high temperatures of from 170 to 250° C. A maximum geraniol/nerol yield of 66.4% at 225 to 235° C. and almost complete conversion of citral is achieved. The citronellol yield was 14.8%. Even at low conversions of about 44%, the yield of the undesired citronellol was still 7.6%, and citronellol selectivity was therefore at about 17%. The selectivities for citronellol reported by Paulose et al. are too high for an economical process for the hydrogenation of citral.

It is an object of the present invention to provide an improved process for the preparation of a ruthenium/iron catalyst supported on carbon, in particular for the selective hydrogenation of olefinically unsaturated carbonyl compounds to give the corresponding unsaturated alcohols, without the disadvantages described above.

The catalyst should have improved catalyst activity and long-term stability, and in particular should lead to high citral conversions and simultaneously low citronellol selectivities when used in the hydrogenation of citral to give geraniol/nerol.

The preparation of the catalyst should avoid the use of corrosive ingredients such as chloride salts and explosive intermediates such as nitrate-saturated carbons.

We have found that this object is achieved by a process for preparing a ruthenium catalyst supported on carbon comprising besides 0.1 to 10% by weight of ruthenium on a carbon support 0.1 to 5% by weight of iron by:

a) suspending the support in water,
b) simultaneously adding the catalytically active components in the form of solutions of their metal salts,
c) simultaneously precipitating the catalytically active components onto the support by addition of a base,
d) separating the catalyst from the aqueous phase of the support suspension,
e) drying the catalyst,
f) reducing the catalyst in a hydrogen stream at from 400 to 600° C., and
g) conditioning the catalyst under low flammability or passivating the catalyst with oxygen.

In the process according to the invention, steps (b) and (c) may be carried out either in succession or simultaneously.

The invention further provides the use of the ruthenium/iron catalyst supported on carbon prepared by the process of the invention for the selective liquid phase hydrogenation of carbonyl compounds of the general formula I

where
$R^1$ and $R^2$ are identical or different and are each independently hydrogen or a saturated or mono- or polyunsaturated straight chain or branched substituted or unsubstituted $C_1$–$C_{20}$-alkyl radical, an unsubstituted or substituted aryl radical or an unsubstituted or substituted heterocyclic group, to give the corresponding unsaturated alcohols of the general formula II

where $R^1$ and $R^2$ are each as defined above.

The carbonyl compounds used may be either saturated or else olefinically unsaturated carbonyl compounds.

A saturated or mono- or polyunsaturated straight-chain or branched $C_1$–$C_{20}$-alkyl radical is, unless otherwise stated, methyl, ethyl, propyl, isopropyl, n-butyl, i-butyl, t-butyl, pentyl, hexyl, heptenyl, octyl, nonyl, decyl, 1-propenyl, 2-propenyl, 2-methyl-2-propenyl, 1-pentenyl, 1-methyl-2-pentenyl, isopropenyl, 1-butenyl, hexenyl, heptenyl, octenyl, nonenyl or decenyl or the radicals corresponding to the components used which are listed below.

An aryl radical is benzyl, phenyl or naphthyl.

A heterocyclic group is, for example, a pyridine, pyrimidine, pyridazine, pyrazine, piperazine, imidazole, furan, oxazole, isothiazole, isoxazole, 1,2,3-triazole or 1,2,4-triazole, thiazole, thiophen or indole ring.

Substituents can be methyl, ethyl, propyl, i-propyl, butyl, t-butyl, fluorine, chlorine, bromine, iodine, nitro or amino.

The saturated carbonyl compounds used are, for example, 3,7-dimethyloctan-1-al and its isomers, tetrahydrogeranylacetone, hexahydrofarnesylacetone, 6-methylheptanone or isovaleraldehyde.

The olefinically unsaturated carbonyl compounds used may be, for example, citronellal, H-geranylacetone, H-nerolidol, methyl vinyl ketone, mesityl oxide, pseudoionone, dihydrofarnesylacetone, lysmeral, methylhexenone, particularly preferably citronellal or else $\alpha,\beta$-unsaturated carbonyl compounds, for example acrolein, methacrolein, crotonaldehyde, prenal, farnesal or citral, particularly preferably citral.

The low flammability liquids mentioned under section (g) of the process according to the invention are liquids having a flash point of greater than 80° C., preferably greater than 100° C., for example water, geraniol, pentanediol, ethylene glycol or nerol or mixtures thereof, particularly preferably geraniol or nerol or mixtures thereof.

Surprisingly, the simultaneous precipitation of the metal salts of the active components ruthenium and iron leads to an improved catalyst activity, selectivity and operating life. The precipitation of the metals in the form of their hydroxides avoids the problems of corrosion or danger of explosion described in the prior art.

Metal salts of the active components ruthenium and iron that can be used include the chlorides, nitrates, nitrosylnitrates, acetates, oxides, hydroxides, and acetylacetonates, preferably the chlorides and nitrates.

The catalyst can be prepared as both a fixed bed and a suspension catalyst by the process of the invention.

The carbon supporting materials are, for example, graphite, carbon black or activated carbon, but preferably activated carbon, e.g. NORIT SX Plus®. Depending on whether the catalyst is to be prepared as a suspension or fixed bed catalyst, the carbon supporting material is used in powdered form or in the form of extrudates, spheres, spall etc. The carbon support can be pretreated before it is doped, such as by oxidation with nitric acid, oxygen, hydrogen peroxide, hydrochloric acid, etc.

The preparation of the catalyst of the invention is described in detail as follows:

The preparation of a suspension catalyst is carried out by suspending the carbon support in water (step (a)) and the support suspension is used in the further process either without further pretreatment, i.e. without the setting of a particular pH, or by setting a pH smaller than 6 using an acid, for example $HNO_3$, or greater than 8 using a base, for example NaOH.

In step (b), the active components ruthenium and iron are added simultaneously in the form of solutions of their metal salts. The addition is preferably carried out at an elevated suspension temperature, particularly preferably at a temperature in the range from 50 to 95° C., more preferably at a temperature of from 70 to 90° C. A base, for example $Na_2CO_3$, $NaHCO_3$, $(NH_4)_2CO_3$, $NH_3$, urea, NaOH, KOH or LiOH, preferably NaOH, is subsequently slowly added in order to precipitate the catalytically active components onto the support and the pH is increased so that it is in the range from 6 to 14, preferably from 8 to 12, particularly preferably to the value of 9 ((c)). The base is preferably added at increased temperature, preferably at a temperature in the range from 50 to 95° C., particularly preferably at a temperature of from 70 to 90° C. The base may also be added at the same time as the metal salt suspension, for instance to maintain the pH of the suspension at a constant level, preferably at a pH of from 8 to 14, more preferably of 9. Since ruthenium and iron are substantially present in the form of their hydroxides after the precipitation, chloride and nitrate anions are washed out to give an unproblematically low content during the washing and separation of the catalyst from the aqueous phase ((d)) following the precipitation.

The filter cake is then dried under reduced pressure or inert gas (e) and the catalyst is reduced in a hydrogen stream, possibly diluted with an inert gas such as nitrogen, at from 400 to 600° C. (f). Finally, the catalyst is either conditioned, e.g. under water or a low flammability liquid, after cooling to temperatures below 40° C. or is passivated using a dilute oxygen stream (about 1% oxygen in an inert gas such as nitrogen) (g).

As an alternative to the process variant described above using gas phase reduction, a wet chemical reduction of the catalyst by addition of a reducing agent such as hydrazine, sodium borohydride, sodium formate, sodium hydrophosphate or formaldehyde can follow the precipitation of the catalytically active component (c). The catalyst is filtered off after the wet chemical reduction, washed and stored moist.

The preparation of the fixed bed catalyst is carried out similarly to the process described for the suspension catalyst, except that in step (a), extrudates, spheres, spall, etc. are used in place of the powdered support material. The characteristic dimensions of these shapes (diameter, length, etc.) are generally above 1 mm. A wet chemical reduction, as previously described, is also possible here instead of gas phase reduction. When the extrudates are dispersed in water, care should be taken to minimize the mechanical stress they are exposed to, in order to minimize attrition. It is advantageous to wash the extrudates with water before use in the catalyst synthesis, in order to separate weakly adhering fine carbon particles.

The catalysts of the invention comprise in general 0.1 to 10% by weight of ruthenium on a carbon support, preferably on activated carbon.

The BET surface area of the catalysts corresponds to the carbon supports used for their preparation, and is in the range from about 100 to 1500, preferably about 800 to 1200 $m^2/g$. The particle size of the ruthenium crystallites generally lies below 10 nm and therefore corresponds to the literature values for ruthenium/carbon catalysts.

The information herein about the % by weight of ruthenium and iron contained in the catalyst is always based on the dry mass of the catalyst.

The catalyst prepared according to the invention has particular importance for the selective hydrogenation of carbonyl compounds, preferably for the selective hydrogenation of unsaturated carbonyl compounds, particularly preferably for the hydrogenation of citral to give geraniol or nerol or of citronellal to citronellol.

The catalyst prepared according to the invention hydrogenates the aldehyde group of the carbonyl compounds with surprisingly high selectivity.

The hydrogenation process can be carried out either continuously or batchwise in suspension or in a fixed bed. The continuous process is particularly advantageous.

The suspension or fixed bed variants may be carried out using the usual reactor designs, as described, for example, in Ullmann's Encyclopedia of Industrial Chemistry, Sixth Edition, 2000 Electronic Release.

The continuous or batchwise suspension process can be carried out as described, for example, in EP 947 943 and U.S. Pat. No. 5,939,589 respectively. The catalyst is used in both the batchwise and the continuous suspension processes in a finely divided form, where the particle size is smaller than 1 mm, preferably in the range from 1 to 100 μm.

The fixed bed variant involves the use of the catalyst in forms customary for fixed bed catalysts, for example in extrudate, spall, tablet or spherical form. Typical extrudate diameters are in the range from 1 to 5 mm, the extrudate length is in the range from 1 to 20 mm. The reaction can be operated using trickle or liquid phase methods.

The reaction is carried out in both the suspension and fixed bed methods at atmospheric or at a pressure within the range from 1 to 200 bar, preferably from 10 to 100 bar, particularly preferably from 20 to 50 bar. The temperatures are in the range from 25 to 200° C., preferably from 60 to 100° C. The reaction can be carried out with or without a solvent. Suitable solvents include lower alcohols such as methanol, ethanol or isopropyl alcohol.

Furthermore, an organic base such as trimethylamine can be used if necessary.

The hydrogenation of the carbonyl compound by the catalyst prepared according to the invention is preferably carried out in the presence of a tertiary amine.

In principle, all tertiary amines are suitable, so that their chemical nature is unimportant, as long as they do not react in other ways with the functional groups of the reaction partners.

For example, the amines named in EP 071 787 are suitable.

The quantity of amine is preferably in the range from 1 to 5% by weight of the quantity of the carbonyl compound used.

The following examples illustrate the invention.

Preparation of Suspension Catalysts

EXAMPLE 1

A) 100 g of activated carbon were mixed with 500 ml conc. $HNO_3$ and stirred at 80° C. for 6 h in a 1 l flask. After cooling, the suspension was filtered and the filter cake was washed with 10 l of distilled water.

The moist carbon was again introduced to the stirred-tank reactor, suspended in 2.5 l of water and heated to 80° C. under reflux cooling. A solution of 13.11 g of ruthenium chloride and 5.15 g of iron chloride in 375 ml of water was then added dropwise with stirring over the course of 120 min. The pH of the suspension after addition of the metal salt solution was 1.4. The pH was increased to 9 by slow dropwise addition of 1 M sodium hydroxide; about 400 ml of NaOH were required for this. Stirring was continued for 1 h and then the suspension was cooled. The catalyst was transferred to a glass suction filter, washed with a total of 40 l of water and dried in a vacuum drying cupboard at 80° C. for 6 h. The dried powder was then reduced in a rotary sphere oven in a stream consisting of 70% $H_2$ and 30% $N_2$ at 500° C. for 3 h. After the end of the reduction, cooling was carried out under nitrogen and the catalyst was passivated with a gas mixture of 1% oxygen in nitrogen. The finished catalyst had a chloride content of under 0.05% by weight. The following contents (% by weight) are furthermore determined: Na: 2.8, Ru: 5.2, Fe: 1.1.

B) The process was carried out as described in A, except that ruthenium nitrosyl nitrate and iron(III) nitrate were used in place of ruthenium chloride and iron chloride. The finished catalyst had a ruthenium content of 5.1% by weight, an iron content of 1.1% by weight and a nitrate content of <0.01% by weight and an Na content of 2.1% by weight.

C) The process was carried out as described in A, except that smaller ruthenium and iron contents were applied to the activated carbon. The finished catalyst had a ruthenium content of 2.8% by weight, an iron content of 0.54% by weight and a chloride content of 0.02% by weight and an Na content of 3.8% by weight.

D) 110 g of the activated carbon Norit SX Plus® were introduced without further pretreatment into a stirred flask with 2 l of water, suspended and heated to 80° C. under reflux. The pH was then raised to 9 by adding aqueous NaOH (1 mol/l). Within one hour, 300 ml of a solution of ruthenium nitrosyl nitrate and iron nitrate (concentration corresponding to 5.85 g of Ru and 1.17 g of Fe) are added dropwise at 80° C. while at the same time maintaining the pH at about 9 by simultaneously adding aqueous NaOH. Stirring was continued at 80° C. for one hour and then the mixture was cooled. The cold suspension was filtered and washed with 40 l of water, then dried in a vacuum drying cabinet at 80° C. for 16 h and reduced and passivated as described under A. The catalyst had an Ru content of 5.0% by weight, an Fe content of 1.0% by weight and an Na content of 0.036% by weight.

E) Comparative example: A catalyst was prepared by the method given in EP 0071787 by saturation of the activated carbon with ruthenium chloride solution, drying, mixing with iron(III) oxide, reduction at 500° C. and conditioning under water.

Testing of the Catalysts Prepared by Methods A to D a) Continuous Suspension Hydrogenation The continuous suspension hydrogenation was carried out in a packed bubble column reactor with product recycling and circulating hydrogen gas (corresponding to EP 947 493).

A liquid mixture of 70% by volume of citral (E/Z≈1), 27% by volume of methanol and 3% by volume of trimethylamine was hydrogenated. The liquid and gas were passed through a packed bubble column (packing volume: 143 ml, packing diameter: 27 mm), each with a throughput rate of about 120 l/h. The citral conversion was adjusted by variation of the pressure, temperature or reactant introduction rate. The pressure was varied in the range from 20 to 40 bar and the temperature in the range from 80 to 100° C.

b) Batchwise Hydrogenation

The batchwise hydrogenation was carried out in an autoclave made by Medimex. The liquid reactant (250 ml of a mixture of 70% by volume of citral (E/Z≈1), 27% by volume of methanol and 3% by volume of trimethylamine) and the catalyst (2.5 g) were introduced to the autoclave before the start of the reaction. The autoclave was then purged at normal pressure with nitrogen. After complete removal of air from the reaction chamber, the addition of nitrogen was ended and the autoclave depressurized. Hydrogen was then introduced into the autoclave and the pressure was set to that required for the reaction. Meanwhile, the temperature was adjusted to that required for the reaction. After the required temperature and pressure had been attained, the stirrer was switched on to start the reaction. During the reaction, samples were taken from the reaction chamber by means of a riser tube. Hydrogenation was carried out at a temperature of 100° C. and a hydrogen pressure at 50 bar.

Result

The results in Table 1 show that the catalysts A to D of the invention are much more active and selective than the comparative catalyst. Particularly at high conversions, considerably more geraniol/nerol and considerably less citronellol is formed. Compared to the comparative catalyst, a lower dry mass of catalyst is required (Examples A and B) or a lower loading with noble metal can be used (Example C) to obtain high conversions. Further, the catalysts of the invention are deactivated more slowly than the comparative catalyst.

Table 2 shows the activity comparison of the catalyst A of the invention with a comparative catalyst from a batchwise hydrogenation experiment. After 50 min, the catalyst A has already achieved almost complete conversion, while the catalyst of the invention has only converted 50% of the citral.

F) A catalyst prepared according to Example 1A) was used for continuous suspension hydrogenation of citronellal (3,7-dimethyloct-7-en-1-al) to citronellol (3,7-dimethyloct-7-en-1-ol). The formation of the fully hydrogenated product 3,7-dimethyloctan-1-ol has to be avoided as far as possible. The reaction was treated with a mixture of 70% citronellal, 27% methanol and 3% trimethylamine. At a reaction temperature of 80° C., a pressure of 20 bar, a reaction feed rate of 2.2 ml/min, a catalyst concentrate of 40 g/(dry) and after 142 h, a citronellal conversion of 94%, a citronellol selectivity of 97.3% and a selectivity for 3,7-dimethyloctan-1-ol of only 1.4% were obtained. The catalyst was notable for its high activity and long-term stability and its high selectivity for citronellol even at high citronellal conversions.

Preparation of Solid Bed Catalysts

EXAMPLE 2

62 g of activated carbon extrudates (Supersorbon SX 30 from Lurgi, diameter 3 mm, surface area about 1000 $m^2\ g^{-1}$) were introduced into a stirred-tank reactor with 400 ml of deionized water and heated to 80° C. with gentle stirring and reflux cooling. A solution of 8.13 g of ruthenium chloride and 3.19 g of iron chloride was added dropwise over 60 min at 80° C. The pH value was then increased to 9 by addition of 1 M sodium hydroxide and stirring was continued for an hour. The catalyst was transferred to a glass suction filter, washed with 10 l of deionized water and then dried at 80° C. for 6 hours in a vacuum drying cupboard. Reduction in a gas mixture of hydrogen and nitrogen (50/4) was then carried out in a reduction oven at 500° C. for 3 hours, followed by cooling to room temperature and passivating with a gas mixture of 1% oxygen in nitrogen.

Catalyst Testing

See also FIG. 1

| Experimental parameters: | |
|---|---|
| Pressure | 40 bar |
| Temperature | 50 to 70° C. |
| Reactor data: | |
| Length: | 470 mm |
| Diameter: | 20 mm |
| Volume: | 150 ml |
| Cat. volume | 100 ml |

TABLE 1

| Catalyst | Dry mass g | Time h | Temperature ° C. | Pressure bar | Reactant addition ml/min | Conversion % | Selectivity Geraniol/Nerol/% | Citronellol/% | Residue/% |
|---|---|---|---|---|---|---|---|---|---|
| A | 40 | 150 | 80 | 20 | 2.2 | 92.4 | 96.8 | 1.2 | 2.0 |
|   |    | 225 | 80 | 40 | 2.2 | 96.1 | 97.6 | 1.6 | 0.7 |
|   |    | 280 | 90 | 40 | 2.2 | 98.6 | 94.6 | 4.3 | 1.1 |
|   |    | 400 | 80 | 20 | 0.7 | 98.6 | 95.2 | 3.0 | 1.8 |
|   |    | 440 | 80 | 20 | 2.2 | 89.8 | 98.1 | 1.3 | 0.6 |
| B | 40 | 170 | 80 | 20 | 2.2 | 91.1 | 97.2 | 1.7 | 1.1 |
|   |    | 240 | 80 | 40 | 2.2 | 95.8 | 96.5 | 2.1 | 1.4 |
|   |    | 310 | 90 | 40 | 2.2 | 96.6 | 96.0 | 2.3 | 1.7 |
|   |    | 350 | 80 | 20 | 2.2 | 88.8 | 97.0 | 1.7 | 1.3 |
| C | 40 | 260 | 80 | 20 | 2.2 | 81.1 | 97.5 | 1.2 | 1.3 |
|   |    | 330 | 90 | 40 | 2.2 | 92.4 | 96.7 | 1.3 | 2.0 |
|   |    | 430 | 100 | 40 | 2.2 | 95.5 | 95.6 | 3.0 | 1.4 |
| D | 40 | 167 | 80 | 20 | 2.2 | 90.9 | 96.1 | 1.4 | 2.5 |
|   |    | 210 | 80 | 40 | 2.2 | 95.7 | 95.7 | 2.5 | 1.8 |
| E | 40 | 140 | 80 | 20 | 1.5 | 84.4 | 94.6 | 2.8 | 2.6 |
|   |    | 170 | 80 | 40 | 1.5 | 93.2 | 94.1 | 4.3 | 1.6 |
|   |    | 815 | 80 | 40 | 2.3 | 75.5 | 96.3 | 1.8 | 1.9 |

TABLE 2

| | Conversion/% | |
|---|---|---|
| Time/min | Comparative Catalyst E | Catalyst A |
| 0 | 0 | 0 |
| 30 | 50 | 98 |
| 60 | 76 | 100 |
| 90 | 90 | 100 |
| 120 | 97 | 100 |
| 150 | 100 | 100 |
| 180 | 100 | 100 |

Description

Citral and a methanol/trimethylamine solution are pumped in separately using piston pumps with balance control. The ratio of citral to methanol to trimethylamine is about 70:27:3. The hydrogen feed is controlled by means of a mass flow regulator. The reactor is operated at from 50 to 70° C. by a liquid phase method. 80% of the reactor effluent is recycled from the liquid phase of the separator by means of a piston pump under buoyant body flow meter control. The remaining product is discharged through a pressure-retaining valve.

General Procedure

The catalyst is installed in the reactor and reduced. The reduction step is carried out at atmospheric pressure with 13 l/h (s.t.p.) of hydrogen by heating to 120° C. After 1 hour, the reactor is cooled. Citral and the trimethylamine/methanol mixture are then introduced separately into the reactor. The parameters are given for each individual run. The analysis is carried out using a 30 m DBWAX 0.32 mm 0.25 µm column (80° C.–3° C./min–230° C.–20 min).

EXAMPLE 3

Solid bed catalyst from Example 2 with recycle: 100 ml (41.1 g) of the catalyst were installed in the reactor and activated as per the general prescription. At a hydrogen pressure of 40 bar (24 l/h, s.t.p.), the addition rates were set as follows: citral (2, 60 g/h, purity 98%), methanol +10% TMA (3, 25.5 g/h), return flow (6, 240 g/h). At a reactor temperature of 75° C. and a conversion of 95.61% (reaction time: 713 h), a selectivity for geraniol/nerol of 95.22% was obtained (ratio of Ger/Ner: 1.20). Byproducts: selectivity for citronellol: 1.80%, selectivity for nerol isomers: 1.70%.

We claim:

1. The process for preparing a ruthenium/iron, catalyst supported on carbon, comprising besides 0.1 to 10% by weight of ruthenium on a carbon support 0.1 to 5% by weight of iron, by:
    a) suspending said support in water,
    b) simultaneously adding the catalytically active components ruthenium and iron in the form of solutions of their metal salts,
    c) simultaneously precipitating the catalytically active components onto the support by addition of a base,
    d) separating the catalyst from the aqueous phase of the support suspension,
    e) drying the catalyst,
    f) reducing the catalyst in a hydrogen stream at from 400 to 600° C., and
    g) conditioning the catalyst under low flammability liquids or passivating the catalyst with a dilute oxygen stream.

2. A process for the preparation of a ruthenium/iron catalyst supported on carbon, comprising besides 0.1 to 10% by weight of ruthenium on a carbon support 0.1 to 5% by weight of iron, by:
    a) suspending said support in water,
    b) simultaneously adding the catalytically active components rutheniumn and iron in the form of solutions of their metal salts,
    c) simultaneously precipitating the catalytically active components onto the support by addition of a base,
    d) reducing the catalyst by addition of an aqueous reducing agent,
    e) separation of the catalyst from the aqueous phase of the support suspension, and
    f) washing the catalyst with water.

3. The process as claimed in claim 1, wherein the catalyst prepared is a suspension catalyst.

4. The process as claimed in claim 1, wherein the catalyst prepared is a fixed bed catalyst.

5. The process as claimed in claim 1, wherein steps (b) and (c) are carried out at a temperature in the range from 50 to 95° C.

6. The process as claimed in claim 1, wherein steps (b) and (c) may be either simultaneous or else in succession.

7. The process as claimed in claim 1, wherein the catalytically active components are used in the form of their chlorides, nitrates, nitrosyl nitrates, acetates, oxides, hydroxides or acetylacetonates.

8. The process as claimed in claim 1, wherein the carbon support can be pretreated by oxidation wit $HNO_3$, oxygen, hydrogen peroxide or hydrochloric acid.

9. The process as claimed in claim 1, wherein the base used to precipitate the catalytically active components on the support is $Na_2CO_3$, $NaHCO_3$, $(NH_4)_2CO_3$, $NH_3$, urea, NaOH, KOH or LiOH.

10. The process as claimed in claim 1, wherein NaOH is used to precipitate the catalytically active components.

11. A process for the selective liquid phase hydrogenation of carbonyl compounds of the general formula I

where
    $R^1$ and $R^2$ are identical or different and are each independently hydrogen or a saturated or mono- or polyunsaturated straight chain or branched substituted or unsubstituted $C_1$–$C_{20}$-alkyl radical, an unsubstituted or substituted aryl radical or an unsubstituted or substituted heterocyclic group, said process comprising the step of reducing said carbonyl compounds, in the presence of a catalyst prepared by the process of claim 1, into corresponding unsaturated alcohols of the general formula II

where $R^1$ and $R^2$ are each as defined above.

12. The process as claimed in claim 11, wherein the carbonyl compound is an α,β-unsaturated carbonyl compound.

13. The process as claimed in claim 11, wherein the carbonyl compound is citral.

14. The process as claimed in claim 11, wherein the carbonyl compound is citronellal.

* * * * *